United States Patent [19]

Furst et al.

[11] Patent Number: 4,562,845

[45] Date of Patent: Jan. 7, 1986

[54] METHODS AND APPARATUS FOR TESTING A BLOOD PRESSURE MONITORING SYSTEM OF THE HYDRAULIC TYPE

[75] Inventors: Emanuel F. Furst; Louis F. Lampe; William L. Woods, all of Tucson, Ariz.

[73] Assignee: The University of Arizona Foundation, Tucson, Ariz.

[21] Appl. No.: 670,208

[22] Filed: Nov. 13, 1984

Related U.S. Application Data

[62] Division of Ser. No. 35,609, May 3, 1979, Pat. No. 4,499,903.

[51] Int. Cl.[4] ............................................. A61B 5/02
[52] U.S. Cl. .................................... 128/675; 73/4 R
[58] Field of Search .............................. 128/672–675, 128/DIG. 12, DIG. 13; 73/4 R

[56]  References Cited

U.S. PATENT DOCUMENTS

| 596,581 | 1/1898 | Edson | 73/4 R |
| 1,869,443 | 8/1932 | Stocklin | 128/DIG. 12 |
| 3,469,578 | 9/1969 | Bierman | 128/DIG. 12 |

Primary Examiner—Kyle L. Howell
Assistant Examiner—Francis J. Jaworski
Attorney, Agent, or Firm—Mason, Kolehmainen, Rathburn & Wyss

[57]  ABSTRACT

The present invention relates to improved apparatus and improved methods for quickly and economically checking the functional performance of blood pressure monitoring systems of the hydraulic type, both prior to and during patient use of the system. More specifically, apparatus faults such as a faulty transducer, and the presence of gaseous bubbles, i.e. air, in the liquid column of such a system through which blood pressure variations of a patient are transmitted to the transducer, are detected and can be isolated as to location in the system by providing volume changing means for changing the volumetric size of a portion or all of the liquid volume containing capacity of the system by a predetermined amount, and indicating or sensing the change in liquid column pressure resulting from the predetermined change in the volumetric size of the liquid volume containing capacity of the system. In accordance with a more specific aspect of the invention, the liquid volume changing means is embodied in and forms a part of one of the liquid containing components of the system, such as the dome which is connected to the transducer, and is provided with a liquid containing reservoir or chamber which overlies and is open to the pressure responsive diaphragm of the transducer.

9 Claims, 12 Drawing Figures

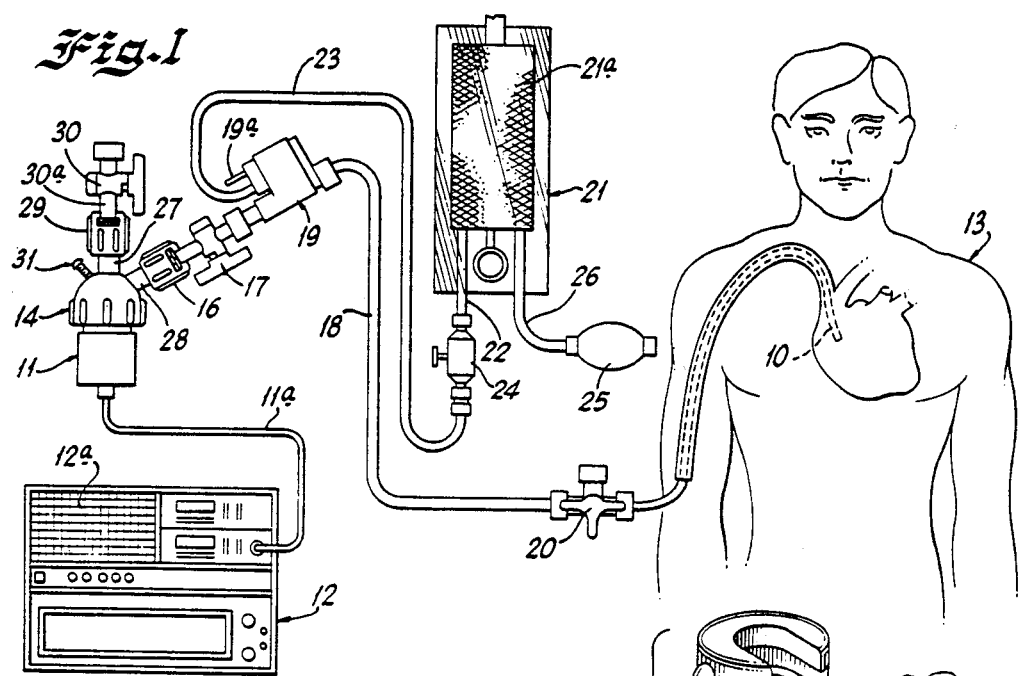
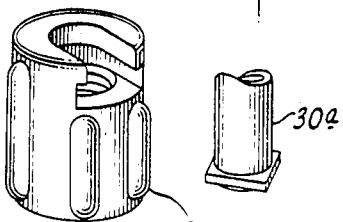
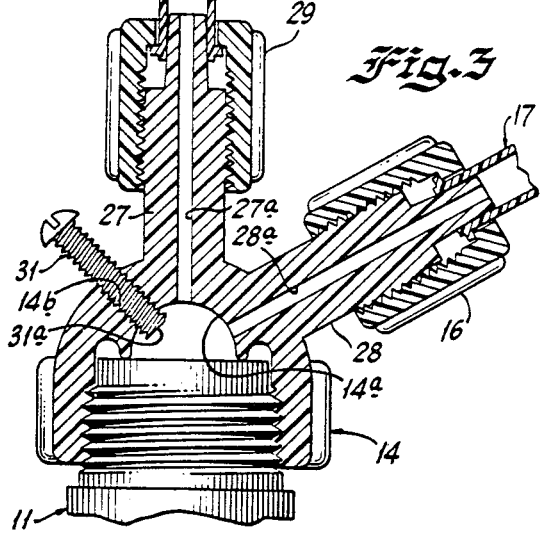
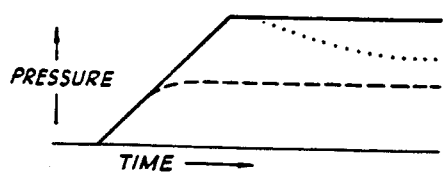
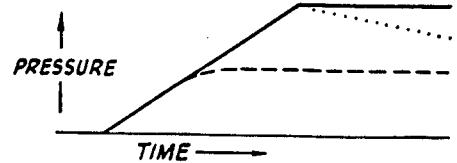

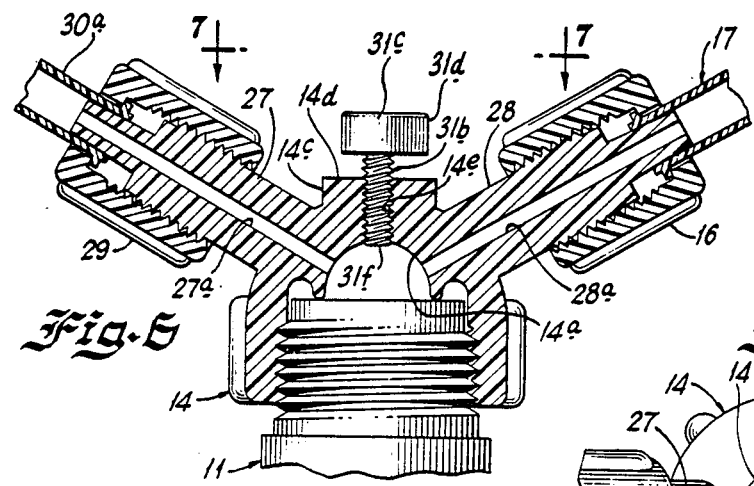
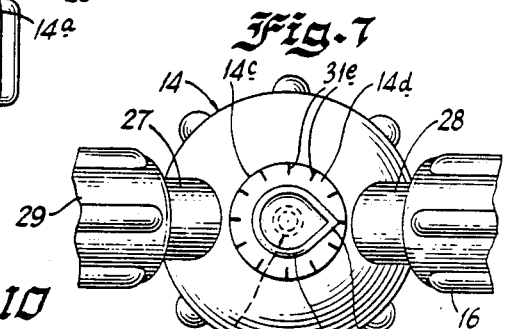
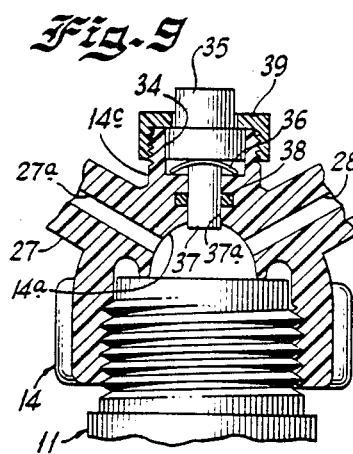
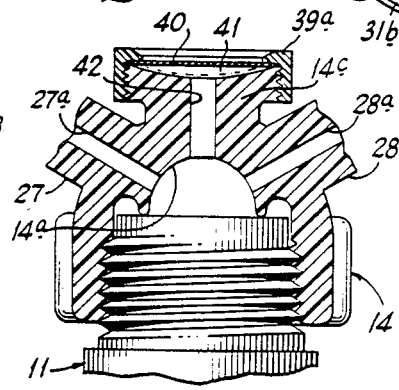
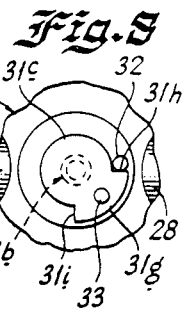
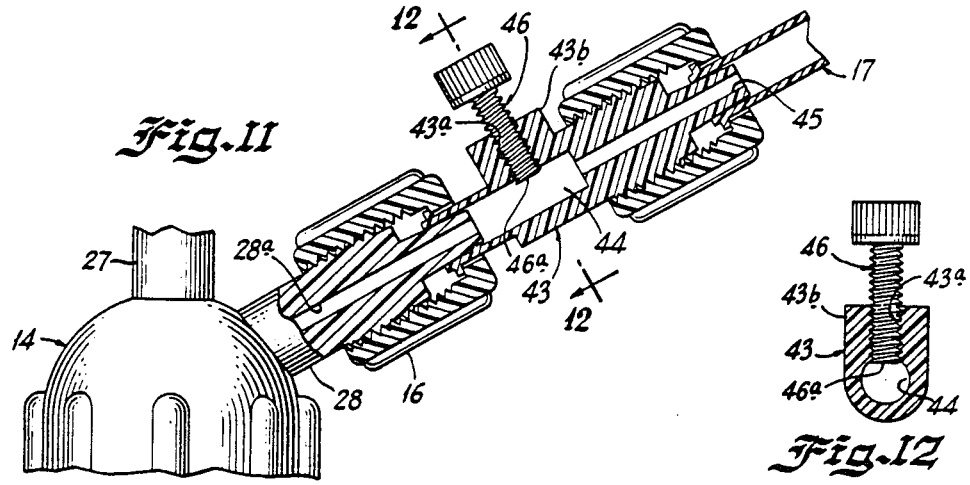
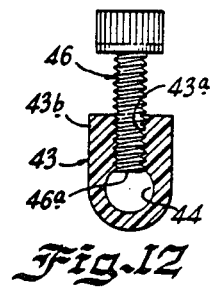

METHODS AND APPARATUS FOR TESTING A BLOOD PRESSURE MONITORING SYSTEM OF THE HYDRAULIC TYPE

CROSS REFERENCE TO RELATED APPLICATION

This is a divisional application of copending patent application Ser. No. 035,609, filed May 3, 1979, now U.S. Pat. No. 4,499,903.

The present invention relates to improvements in blood pressure monitoring systems of the hydraulic type and more particularly to improved apparatus and improved methods for quickly and economically checking the functional performance of such a system, both prior to and during a patient blood pressure monitoring operation.

In blood pressure monitoring systems of the indicated type, blood pressure variations of a patient are obtained by inserting a catheter into a blood vessel or heart cavity of the patient and sensing the blood pressure variations of the patient by means of a pressure sensitive transducer which is remotely located from but connected to the catheter. A tube and dome contained liquid column typically serves to couple the blood being pumped through the patient's body with the pressure responsive element of the transducer. The transducer responds by converting the resulting movement of its pressure responsive element into an electrical signal which is capable of being translated into any one of a variety of visually observable displays, such, for example, as by means of a cathode ray tube, a chart recorder, a meter or the like.

In systems of the character described, unusual or abnormal pressure indications can be the result of apparatus faults, the patient's physical state, or both. One particularly troublesome problem can be attributed to the presence of air bubbles in the liquid column which couples the patient's blood to the pressure sensitive element of the transducer. These bubbles have the effect of distorting the observed pressure indications. Another common problem not infrequently resides in malfunctioning of the transducer which will fail to convert a given pressure change into an equivalent electrical signal change, so that a false pressure indication is given to the observer, usually a nurse.

It is vital to be able to identify and isolate such system problems quickly so that appropriate medical ministrations to the patient may be promptly initiated, if necessary. One common trouble shooting technique presently used is to replace the suspected transducer with a sterile replacement and see if the apparent problem still exists. This is an expensive and time consuming operation. Another approach to the solution of such problems is to set up a second, sterile liquid column system in parallel with the suspected system. If the problem then disappears, the parallel system is used, but again this technique is both time consuming and expensive. Moreover, it is not definitive of the problem. A third approach is to pressurize the liquid column with air, observe the increased liquid pressure of the column with a mercury manometer and compare the manometer pressure indication with that given by the transducer energized display unit. This also is a time consuming and expensive checking procedure. All of the above described checking procedures may fail to identify the source of a given problem and certain thereof result in compromising the sterility of one or more components of the system, thus greatly increasing the cost of operating and maintaining such systems.

It is an object of the present invention to provide improved methods and apparatus for obviating the above described difficulties experienced in operating and maintaining blood pressure monitoring systems of the hydraulic type.

It is another object of the invention to provide improved methods and improved apparatus for enabling a health professional team, non-skilled in the equipment aspects of blood pressure monitoring systems, quickly, confidently and repeatedly to test the functional status of a hydraulic blood pressure monitoring system, both before the system is placed in use and during its use, without compromising the sterility of the system and without calling for technical assistance.

It is a further object of the invention to provide an improved method for identifying the presence of gaseous bubbles in the liquid column of a blood pressure monitoring system of the hydraulic type.

It is a still further object of the invention to provide an improved method and improved apparatus for determining the approximate location of gaseous bubbles in the liquid column of a hydraulic blood pressure monitoring system.

Still another object of the invention is to provide an improved method and improved apparatus for identifying a faulty transducer when the transducer is embodied in a blood pressure monitoring system of the hydraulic type.

It is still another object of the invention to provide an improved liquid receiving structure which is adapted to contain liquid forming a part of the liquid column of a hydraulic blood pressure system and the volumetric capacity of which can be easily changed by a predetermined amount prior to or during use of the system, thereby to change the liquid column pressure by a predetermined amount.

The invention, both as to its organization and method of operation, together with further objects and advantages thereof, will best be understood by reference to the following specification taken in connection with the accompanying drawings, in which:

FIG. 1 is a diagrammatic representation of a typical hydraulic blood pressure monitoring system modified to incorporate the features of the present invention;

FIG. 2 is an exploded view, partially in section, illustrating the parts of the liquid receiving vessel or dome forming a part of the system shown in FIG. 1;

FIG. 3 is a sectional view taken through the dome illustrated in FIG. 2;

FIGS. 4 and 5 are reproductions of cathode ray tube traces illustrating the mode of operation of the present improved system;

FIG. 6 is a sectional view illustrating a modified embodiment of the dome;

FIG. 7 is an enlarged partial top view of the dome shown in FIG. 6;

FIG. 8 is a top plan view illustrating the stop mechanism which may optionally be embodied in the dome shown in FIG. 6;

FIG. 9 is a sectional view illustrating a further embodiment of the dome structure;

FIG. 10 is a sectional view illustrating still another embodiment of the present improved dome structure;

FIG. 11 is a sectional view illustrating a different arrangement for changing the liquid volume containing capacity of a hydraulic blood pressure monitoring system; and FIG. 12 is a sectional view taken along the lines 12—12 in FIG. 11.

Referring now to the drawings and more particularly to FIG. 1 thereof, the invention is there illustrated in its embodiment in a blood pressure monitoring system of the hydraulic type which comprises a catheter 10, a pressure sensitive transducer 11 and an electronic pressure indicating unit 12 of conventional design which is adapted to convert an electrical signal generated by the transducer 11 into a visual trace or display which depicts pressure variations sensed by the transducer 11. Typically, this unit is provided with a cathode ray display tube, the face of which is indicated at 12a, which functions to portray the sensed pressure variations as a visually observable trace.

As shown, the catheter 10 is passed into one of the heart chambers, such as the left atrium, of a patient 13 through a main blood vessel or artery of the patient so that the open end thereof is exposed to blood pressure variations at this point in the cardiovascular system of the patient. The pressure sensitive transducer 11, which may be of any desired commercial type, is equipped at its upper open end, as illustrated in FIGS. 1 and 3, with a pressure responsive diaphragm, not shown, which moves up and down in response to variations in the pressure exerted thereon. Movement of this pressure responsive diaphragm is translated into a varying electrical signal by means of strain gauges or the like which may serve to vary the setting of a bridge circuit of any appropriate type. This varying electrical signal, which is or should be faithfully representative of the pressure exerted upon the diaphragm of the transducer, is transmitted over a cable 11a to the pressure indicating unit 12 where it is electronically or electromechanically converted into a visually observable indication or display.

As in all commercially available blood pressure monitoring systems of the hydraulic type, the varying pressure source, namely the blood which is being pumped through the patient's body by the patient's heart, is coupled to the pressure responsive diaphragm of the transducer 11 from the body free end of the catheter 10, through a non-compressible liquid column which is contained within flexible tubing and other devices interconnecting the top of the transducer 11 and the body free end of the catheter 10. More specifically, the liquid column containing components of the system comprise a hollow vessel or dome 14 which connects with an open-shut valve or stopcock 17 through a coupling assembly 16, a continuous flush device 19, a tubing section 18, and a second open-shut valve or stopcock 20 to which the body free end of the catheter 10 may be directly connected or alternatively may be connected through a third tubing section. The tubing sections used in the system, while flexible, are substantially non-expansible by pressure variations in those portions of the liquid column contained therewithin, so that the volume of liquid contained in these tubing sections remains constant during use of the system. The continuous flush device 19 may be of the type commercially sold as the Sorensen Intraflo. It is supplied with charging liquid from a pressure cuff and infusion device 21 through tubes 22 and 23 and a clamp type valve 24. More in detail, liquid for charging the liquid column and for feeding an anti-coagulant, such as Heparin, into the catheter 10 is supplied to the continuous flush device 19 through the tubes 22 and 23 from a collapsible plastic bag, not shown, which is contained within and enclosed by the pressure cuff 21a of the device 21. This cuff is adapted to be inflated to pressurize the liquid containing plastic bag by means of the usual pressurizing bulb 25 which is connected to the cuff 21a by means of a flexible tube 26. Conventionally, the Sorensen Intraflo device 19 is provided with facilities for continuously feeding a small quantity of the anti-coagulant solution into the catheter 10 to prevent the catheter from becoming clogged with coagulated blood. This device is also provided with a self-restoring valved by-pass passage through which liquid from the supply bag may be discharged into the above described liquid column containing components of the system and through which the liquid may rapidly flow in order to flush these components. The self-restoring valve located in this passage is normally closed, but may be opened by pulling on a valve actuating tab 19a forming part of the device 19.

As best shown in FIGS. 2 and 3 of the drawings, the vessel or dome 14 is provided with two threaded outwardly projecting male connecting parts 27 and 28 having liquid passageways or bores 27a and 28a, respectively, extending throughout the lengths thereof. The part 27 is connected by means of an internally threaded coupling element 29 to the lower open end 30a of a flushing valve or stopcock 30, the other end of which is open to the atmosphere. The other connecting part 28 is conntected either directly or indirectly to one open end of the valve or stopcock 17 by means of the coupling element 16. The dome 14 is usually molded from a clear plastic material and in use in many hospitals it is a disposable or throw-away item since the cost of sterilization after use may exceed the cost of replacing the component by a factor of as much as two to one.

Internally, the dome is provided with a somewhat enlarged liquid reservoir or chamber 14a which overlies the pressure responsive element of the transducer 11 and is adapted to contain liquid forming a part of the above described liquid column. As will be understood, the liquid within the chamber 14a covers and impinges upon substantially the entire upper surface of the pressure responsive diaphragm of the transducer 11. As shown in FIG. 3, a threaded connection is used to provide a sealed connection between the upper, pressure responsive end of the transducer 11 and the dome 14.

In accordance with one aspect of the present invention, the walled structure or dome 14 defining the liquid receiving chamber 14a is provided with an opening therethrough, and adjustable means cooperating with this opening are provided for changing the liquid volume capacity of the chamber 14a by a predetermined amount. In the embodiment of the invention illustrated in FIGS. 1, 2 and 3 of the drawings, the wall opening is indicated at 14b and the volume adjusting means which cooperates with this opening is in the form of a machine screw 31. More specifically, the threaded screw 31 mates with the internal threads of the opening 14b so that the extent of penetration of the screw end 31a into the chamber 14b can be adjusted as desired. It will be apparent that the pitch of the mating threads determines the degree of penetration of the screw end 31a into the chamber 14a for a given angle of rotation, such as one full turn, of the screw 14. Movement of the screw end 31a into the chamber or reservoir 14a has the effect of decreasing the liquid volumetric capacity of this chamber by an amount related to the diameter of the screw and the thread pitch. This decrease in the liquid volume capacity of the chamber 14a results in a related increase in the pressure of the inelastic liquid column of the system and that portion thereof which bears against the pressure responsive element of the transducer 11, which in turn causes an increase in the pressure indicated by the unit 12 in the manner move fully explained below.

In setting up the above described system for patient use, connections are made between the various components of the system in the usual manner. These hydraulic connections should be sufficiently firm or tight so that when liquid is injected into the system to form the hydrostatic liquid column, the liquid column is completely sealed from the atmosphere. Moreover, the apparatus should be so positioned that the top end of the stopcock 30 is substantially level with the left atrium of the patient's heart.

To charge the system with liquid and thus form the liquid column through which blood pressure variations within the patient 13 are to be transmitted to the transducer 11 after connection to the catheter 10, the pressurizing bulb 25 is repeatedly activated until a pressure of about 300 m.m. of mercury is exerted by the cuff 21a of the unit 21 on the liquid bag contained therewithin. The stopcocks or valves 17, 30 and 20 are then opened, following which the valve actuator tab 19a is pulled to permit the pressurized liquid to flow from the bag within the unit 21 into the described components of the system. During this filling operation, all parts of the system, including the tube sections and the dome reservoir 14a, as well as the catheter 10, are filled with liquid, and air is theoretically expelled from these parts of the system. When liquid starts to flow out of the top of the stopcock 30, the desired liquid column is supposedly established and this stopcock is then closed.

In order to establish the desired datum or datum pressure trace or indication on the display screen 12a of the indicating unit 12, the stopcock 17 is closed and the stopcock 30 is opened. This subjects the pressure sensitive diaphragm of the transducer 11 to the prevailing atmospheric pressure. The electronics of the indicating unit 12 may now be adjusted in the usual manner to establish a zero reference or datum pressure indication by the display screen 12a or other metering device or indicator. After zeroing the reference or datum pressure indication, the stopcock 30 is closed, and the stopcock 20 is connected to the body free end of the catheter 10 which is now filled with blood. The system is now ready to be flushed and checked using the present improved checking methods.

In accordance with one aspect of the present invention, the pressure sensing fidelity of the transducer 11 may be checked either before or during patient use by closing the stopcock 17 to block off that portion of the system between this stopcock and the pressure sensitive diaphragm of the transducer 11 and by changing the liquid volume containing capacity of the blocked off portion of the system by a predetermined amount. More specifically, with the stopcocks 17 and 30 closed, the volume changing screw 31 is rotated through a predetermined angle, such as ninety or one hundred and eighty degrees, or more, to project the end 31a of this screw into the dome 14 to decrease the volume of the chamber 14a by a predetermined amount. This decrease in the liquid holding capacity of the reservoir 14a results in a predetermined increase in the pressure exerted by the blocked off portion of the liquid column on the pressure sensitive diaphragm of the transducer 11. The predetermined pressure increase on the transducer diaphragm should manifest itself as a corresponding increase in the pressure indicated by the pressure indicating screen 12a of the unit 12 as shown by the solid line pressure indicating trace depicted in FIG. 4 of the drawings. If, however, the transducer 11 is malfunctioning, or if leaky connections exist in that part of the system to the left of the stopcock 17 as shown in FIG. 1, or if a gaseous bubble is present in the blocked off portion of the system, the displayed pressure trace will indicate a somewhat lower pressure, as depicted by the dotted or dashed line traces of FIG. 4 for example. Leaky connections can usually be located and corrected by visual and touch examination of the system component connections.

More specifically, and as a further check, if one or more leaky connections is present in the blocked off portion of the system, the pressure indication will rise to the maximum dotted line value shown in FIG. 4 and will gradually fall as liquid escapes from the system through the leaky connection or connections. The dotted line pressure trace is typically representative of such a condition. On the other hand if one or more gaseous bubbles is present in the system or if the transducer 11 is not functioning properly, the pressure indication will rise to the dashed line value shown in FIG. 4 and stay at this value.

In order to discriminate between a malfunctioning transducer 11 and the presence of one or more gaseous bubbles, i.e. air, in the blocked off portion of the system, the volume changing screw 31 is restored to its initial setting and the system is flushed by maintaining the valve 20 closed, opening the valves 17, 24 and 30, and pulling the valve tab 19a, thus permitting liquid to flow from the pressurized bag within the unit 21 through the system, including the reservoir or chamber 14a, and out the open end of the stopcock 30. While this flushing operation is under way, the various liquid containing components of the system, particularly the dome 14, should be lightly tapped in order to detach gaseous bubbles from the internal surfaces of these components and permit the bubbles to be flushed out of the system. After the flushing operation is completed, valve 30 is closed, the valve pull tab 19a is released. If the meter now reads about 300 mmHg, the transducer is good; if not, it is bad. Valve 17 is then closed. The volume decreasing operation is now repeated by again rotating the volume changing screw 31 to its decreased volume setting. If the lower than normal pressure indication given by the display portion 12a of the unit 12 still persists, the operator is informed that bubbles still remain in the dome and that the flushing operation should be repeated. On the other hand, if the expected predetermined increase in pressure is indicated, the operator is informed that the transducer 11 is functioning normally and further that the trouble was attributable to the presence of one or more gas bubbles in the blocked off portion of the system, probably the chamber 14a of the dome 14. As will be understood from the foregoing explanation, if the expected higher pressure reading is obtained, the volume changing screw 31 is retracted to its normal maximum volume setting.

In order to determine whether or not there are faulty, i.e. leaky, connections in the overall system, or that gaseous bubbles are present in that portion of the liquid column which extends between the stopcocks 17 and 20, the stopcocks 20 and 30 and the valve 24 are maintained in their closed settings, the stopcock 17 is opened, and the volume changing screw 31 is again rotated through a predetermined rotational angle to its minimum volume setting. As a result liquid volume capacity of the system between the transducer diaphragm and the stopcock 20 is reduced by a predetermined amount. This should result in an increase in the indicated pressure by the amount shown in solid lines in FIG. 5 of the drawings. However, if the pressure only rises by the amount shown in dotted lines in FIG. 5, and then starts to fall the operator is informed that leaky component connections are present in the system. Alternatively, if the pressure indication rises to the dashed line position shown in FIG. 5 and stays level, an indication is provided that gaseous bubbles are present in that portion of the system extending between the stopcocks 17 and 20. As explained above, the location of leaky connections can usually be accomplished by visual and touch inspection of the connection assemblies to determine whether they are wet or dry. If the lower pressure reading can be attributed to the presence of gas bubbles in that portion of the system between the stopcocks 17 and 20, one or more additional system flushing operations should be instituted. These flushing operations are performed in the manner explained above, either toward the catheter 10 or the reservoir 14a. After each flushing operation, a pressure check is carried out in the above described manner by manual manipulation of the volume changing screw 31.

Once the system is found to be in satisfactory working condition, the volume changing screw 31 is reset to its maximum volume setting and the system is ready to respond to the blood pressure fluctuations in the cardiovascular system of the patient 13. During use, the stopcock 20 is, of course, connected to the body free end of the catheter 10 and is opened, the stopcock 17 is opened, the valve 24 is opened and the stopcock 30 is closed. This exposes the liquid column of the system to the blood being pumped through the patient by the patient's heart, with the result that variations in the patient's blood pressure are transmitted through the liquid column, converted into a varying electrical signal by the transducer 11, and translated into an observable blood pressure indication by the indicating unit 12.

It will be understood from the foregoing explanation that a person unskilled in the technical aspects of the system, such as a nurse, can easily perform the above described system checking procedures. It will also be understood that these procedures can be easily and quickly performed while the system is in patient use. Thus, by simply turning the stopcock 20 to its closed position, the blood flow in the patient 13 is isolated from the liquid column of the system, thereby permitting any or all of the above described system checks to be performed without disturbing the patient.

In the alternative embodiment of the present improved dome 14 illustrated in FIGS. 6 and 7 of the drawings, the connecting parts 27 and 28 thereof are flared away from each other to provide a centrally located platform part 14c through which the reservoir volume changing screw 31b extends. More particularly, the platform part 14c is provided with a flat upper surface 14d and has a threaded opening 14e extending vertically therethrough which matingly engages the threads of the screw 31b. At its upper end, the screw 31b carries an enlarged finger manipulable dial-like head 31c having a pointer end 31d which is adapted to cooperate with a circular scale 31e to indicate the angular setting of the screw 31b and hence the extent of penetration of the screw end 31f into the reservoir or chamber 14a. As will be understood from the above description, rotation of the head 31c in the proper direction and by an amount measurable through the observable relationship between the pointer end 31d and the scale 31e results in penetration of the screw end 31f into the reservoir or chamber 14a to produce a predetermined decrease in the liquid volume capacity of the chamber 14a.

For the purpose of defining predetermined limits in the permissible angular rotation of the screw 31b, the arrangement illustrated in FIG. 8 of the drawings may optionally be employed. As there shown, the screw head 31c is provided with a stop segment 31g which may be finger actuated to rotate the screw 31b between its maximum and minimum reservoir volume settings. It will be understood that with this arrangement, the magnitude of change in the liquid volume capacity of the reservoir or chamber 14a, for a given screw diameter and thread pitch, is determined by the width of the stop segment 31g and hence the angular displacement between the stop surfaces 31h and 31i.

Referring now to FIG. 9, a further embodiment of the present improved dome 14 is there shown. In this embodiment, the platform part 14c is of increased height and is provided with a circular recess 34 extending downwardly from the top surface thereof for receiving a pushbutton 35, a uni-stable concave spring 36 and the upper end of a volume changing plunger 37. In more detail, the plunger 37 extends through an opening 37a in the dome part 14c and is encircled by a compressible sealing ring 38. At its upper end, the plunger 37 is fixedly connected to the spring 36 so that when the button 35 is depressed and then released, the spring 36 will return the plunger 37 to its retracted position. An inverted cup-shaped cap 39 threaded onto the threaded upper end of the dome part 14 is employed to retain the component parts of the dome in assembled relationship.

In operation, when the pushbutton 35 is depressed from its illustrated retracted position, the plunger 37 is moved downward to project the lower end thereof into the chamber 14a and thus produce the desired predetermined change, i.e. decrease, in the liquid volume capacity of the chamber 14a. Such downward movement of the plunger 37 is limited through contact of the under surface of the spring 36 with the surface defining the bottom of the recess 34. When the button 35 is released, the spring 36 functions to restore the elements 35 and 37 to their normal retracted settings. It will be understood that the sealing ring 38 serves to prevent air from entering the chamber 14a and to prevent liquid from escaping from this chamber.

The dome assembly of FIG. 9 may be simplified to some extent by employing the modification illustrated in FIG. 10 of the drawings. As there shown, a resilient diaphragm 40 is sealingly clamped around its edges between the top edge of the dome part 14c and the internally extending flange of the cap 39a. The reservoir 14a communicates with a small liquid receiving chamber 41 located directly beneath the diaphragm 40 through an opening 42 formed centrally through the dome part 14c. The chamber 41 is formed by providing a concave depression in the top surface of the dome part 14c so that when the resilient diaphragm 40 is depressed at its center, the lower surface of the diaphragm is brought into contact with the surface of the concave depression to stop further downward movement of the diaphragm and to expel all liquid from the chamber 41.

When used in the system shown in FIG. 1, all cavities within the dome structure shown in FIG. 10 are filled with liquid. Thus the normal liquid receiving capacity of the FIG. 10 structure includes the liquid holding volume of the chamber 14a, the chamber 41 and the bore or opening 42, all of which are filled with liquid during use of this structure. This liquid holding capacity is reduced by the predetermined amount represented by the holding capacity of the chamber 41 when the diaphragm 40 is fully depressed to engage the concave upper surface of the dome top part 14c. Obviously, this cavity is restored to its normal liquid receiving size when the pressure on the diaphragm 40 is removed thus permitting this diaphragm to return to its normal position shwon in FIG. 10 of the drawings.

As an alternative to the above described dome structures, the volume changing device 43 illustrated in FIGS. 11 and 12 of the drawings may be employed to change the liquid volume capacity of the system shown in FIG. 1 by the desired predetermined amount. Briefly, this device is of tubular form and at its right end as viewed in FIG. 11 is provided with a threaded male coupling part which is compatible with the female coupling part of the stopcock 17, for example, to form a sealed connection between the stopcock and the device 43. At its left end, the device 43 is provided with a female coupling part which is compatible with the male coupling part 28 of the dome shown in FIGS. 1, 2 and 3 to form a sealed connection between the dome 14 and the device 43. Internally, the device 43 is provided with an enlarged cavity 44 which is open to a smaller bore 45 leading to the stopcock 17. In order to change the liquid holding volume of the cavity 44 by the desired predetermined amount, a volume changing screw 46 is provided, the threads of which are matingly engaged with the internal threads of an opening 43a formed in the thickned upper wall 43b of the device. As will be understood from the preceding explanation, rotation of the screw 46 in the proper direction results in movement of its end 46a into the cavity or chamber 44 to reduce the liquid volume capacity of this cavity and hence of the hydraulic blood pressure monitoring system in which the device is included. Thus, by rotating the screw 46 between predetermined angular limits, the liquid holding capacity of the system may be correspondingly changed between the desired predetermined limits. One advantage characterizing the device 43 is that it may be used in combination with domes of conventional commercial construction to achieve the system checking advantages described above.

What is claimed is:

1. A method of determining the presence of apparatus faults or the presence of gaseous bubbles in a liquid column of a blood pressure monitoring system of the hydraulic type wherein a pressure sensitive element is disposed in fluid communication with said liquid column and said liquid column is in fluid communication with a circulatory system of a patient wherein blood pressure variations of a patient are sensed through said liquid column at a point remote from the patient, which comprises inserting a solid member into a portion of said liquid column defined between said pressure sensitive element and said patient to change the volumetric size of said liquid column portion by a predetermined amount, and indicating the change in the liquid column pressure pattern resulting from said change in the volumetric size of said liquid column portion.

2. A method of determining the presence or absence of faults in a blood pressure monitoring system of the hydraulic type wherein a pressure sensitive element is disposed in fluid communication with aaid liquid column and said liquid column is in fluid communication with a circulatory system of a patient wherein blood pressure variations of a patient are sensed at a point remote from a point of catheter contact with a circulatory system of a patient through the liquid column of the system, which comprises inserting a solid member into a portion of said liquid columm defined between said pressure sensitive element and said patient to change the volumetric size of said liquid column portion by a predetermined amount, and indicating the change in the liquid column pressure resulting from said change in the volumetric size of said portion of said system.

3. A method of checking the pressure sensitive fidelity of a pressure sensitive transducer having a pressure sensitive element embodied in a blood pressure monitoring system of the hydraulic type wherein a pressure sensitive element is disposed in fluid communication with said liquid column and said liquid column is in fluid communication with a circulatory system of a patient wherein blood pressure variations of a patient are sensed through the liquid column of the system by the pressure responsive element of said transducer at a point remote from the point of a catheter contact with the circulatory system of the patient, comprising isolating from fluid communication with the circulatory system of the patient a portion of the liquid column in fluid communication with said pressure responsive element of said transducer, changing the volumetric size of the isolated portion of said liquid column, and indicating the change in liquid column pressure sensed by said transducer as a result of said change in the volumetric size of a said isolated portion of said system.

4. A method of determining the presence of gaseous bubbles in a liquid column of a blood pressure monitoring system of the hydraulic type wherein a pressure sensitive element is disposed in fluid communication with said liquid column and said liquid column is in fluid communication with a circulatory system of a patient wherein blood pressure variations of a patient are sensed through said liquid column at a point remote from the patient, which comprises inserting a solid member into a portion of said liquid column defined between said pressure sensitive element and said patient to change the volumetric size of said liquid column portion by a predetermined amount, and indicating the change in the sensed liquid column pressure resulting from said change in the volumetric size of said liquid column portion of said system.

5. A liquid receiving device for communicating a portion of the liquid column of a blood pressure monitoring system of the hydraulic type, wherein a pressure sensitive element is disposed in fluid coupling with said liquid column and said liquid column is in fluid communication with a circulatory system of a patient, comprising a walled structure having a liquid receiving chamber, said walled structure including an opening through a wall thereof communicating said chamber, and an adjustable volume changing solid member cooperating with said opening and capable of insertion into and removal from said liquid receiving chamber a predetermined amount for changing the liquid volume capacity of said liquid receiving chamber a predetermined amount without simultaneously causing a change in volume in said liquid column.

6. The liquid receiving device of claim 5, wherein said opening through said wall is threaded and wherein said adjustable volume changing solid member comprises a threaded element adapted to be threaded into and out of said opening to change the liquid volume capacity of said chamber.

7. A liquid reservoir for use in a hydraulic blood pressure monitoring system of the hydraulic type wherein a pressure sensitive element is disposed in fluid communication with a liquid column and said liquid column is in fluid communication with a catheter connected to a circulatory system of a patient, comprising a walled structure defining a liquid receiving chamber, said walled structure including an opening therethrough and having an open side adapted to be closed by said pressure sensitive element, and an adjustable volume changing solid member received within said opening and capable of insertion into and removal from said liquid receiving chamber a predetermined amount for changing the liquid volume capacity of said liquid receiving chamber a predetermined amount.

8. The liquid reservoir of claim 7, wherein said opening is threaded and wherein said adjustable volume changing solid member comprises a threaded element adapted to be threaded into and out of said opening to change the liquid volume capacity of said chamber a predetermined amount.

9. The liquid reservoir of claim 7, including indicating means in operable communication with said pressure sensitive element for indicating the degree of adjustment of said volume changing means.

* * * * *